(12) United States Patent
Hiroyasu

(10) Patent No.: US 11,046,016 B2
(45) Date of Patent: Jun. 29, 2021

(54) ULTRASONIC WELDING DEVICE AND ULTRASONIC WELDING METHOD

(71) Applicant: ZUIKO CORPORATION, Settu (JP)

(72) Inventor: Masato Hiroyasu, Settu (JP)

(73) Assignee: ZUIKO CORPORATION, Settu (JP)

( * ) Notice: Subject to any disclaimer, the term of this patent is extended or adjusted under 35 U.S.C. 154(b) by 344 days.

(21) Appl. No.: 16/312,110

(22) PCT Filed: Jun. 19, 2017

(86) PCT No.: PCT/JP2017/022591
§ 371 (c)(1),
(2) Date: Dec. 20, 2018

(87) PCT Pub. No.: WO2018/012210
PCT Pub. Date: Jan. 18, 2018

(65) Prior Publication Data
US 2019/0160757 A1    May 30, 2019

(30) Foreign Application Priority Data
Jul. 11, 2016    (JP) .............................. JP2016-137064

(51) Int. Cl.
*B23K 20/00*    (2006.01)
*B29C 65/08*    (2006.01)
(Continued)

(52) U.S. Cl.
CPC ........ *B29C 65/08* (2013.01); *A61F 13/15739* (2013.01); *A61F 13/49* (2013.01); *B23K 20/10* (2013.01)

(58) Field of Classification Search
CPC ............. H01L 2924/00; H01L 2224/78; H01L 2224/78268; H01L 2224/78301;
(Continued)

(56) References Cited

U.S. PATENT DOCUMENTS 3,436,958 A * 4/1969 Proctor ................ G01N 29/348
73/600
2002/0195473 A1* 12/2002 Fournier ................... B60R 9/10
224/502
(Continued)

FOREIGN PATENT DOCUMENTS

JP    2010-214946 A    9/2010
JP    2017-104288 A    6/2017
(Continued)

OTHER PUBLICATIONS

PCT/ISA/210, "International Search Report for International Application No. PCT/JP2017/022591," dated Aug. 1, 2017.

*Primary Examiner* — Erin B Saad
(74) *Attorney, Agent, or Firm* — Manabu Kanesaka

(57) ABSTRACT

An ultrasonic welding device includes a support device configured to support a work piece along a predetermined conveyance surface; a welding machine including an oscillator for generating a high-frequency electric signal, a transducer for converting the high-frequency electric signal to a mechanical vibration, and a horn to which the mechanical vibration is transmitted, the horn being disposed to face a part to be welded of a work piece supported along the conveyance surface, and the mechanical vibration being imparted via the horn to the part to be welded, whereby the part to be welded is welded; a detector for detecting an abnormality in the part to be welded, the detector being disposed upstream in the conveyance direction of the work piece than the support device; and a protective device for prohibiting the welding machine from welding the part to be welded in which an abnormality is detected by the detector.

20 Claims, 10 Drawing Sheets

(51) Int. Cl.
*A61F 13/49* (2006.01)
*B23K 20/10* (2006.01)
*A61F 13/15* (2006.01)

(58) Field of Classification Search
CPC .... B23K 20/10; B23K 20/106; B23K 1/0008;
B23K 2101/40
See application file for complete search history.

(56) References Cited

U.S. PATENT DOCUMENTS

| | | | | |
|---|---|---|---|---|
| 2004/0103302 A1* | 5/2004 | Yoshimura | ............... | G06F 21/86 |
| | | | | 726/27 |
| 2010/0224327 A1* | 9/2010 | Jalbert | .................... | B29C 65/08 |
| | | | | 156/378 |
| 2012/0186349 A1* | 7/2012 | Inoue | ................. | G01N 29/4454 |
| | | | | 73/600 |
| 2016/0254215 A1* | 9/2016 | Sato | ................... | H01L 21/4871 |
| | | | | 257/668 |

FOREIGN PATENT DOCUMENTS

| | | | |
|---|---|---|---|
| WO | 2014/200102 A1 | 12/2014 | |
| WO | 2014/200104 A1 | 12/2014 | |

\* cited by examiner

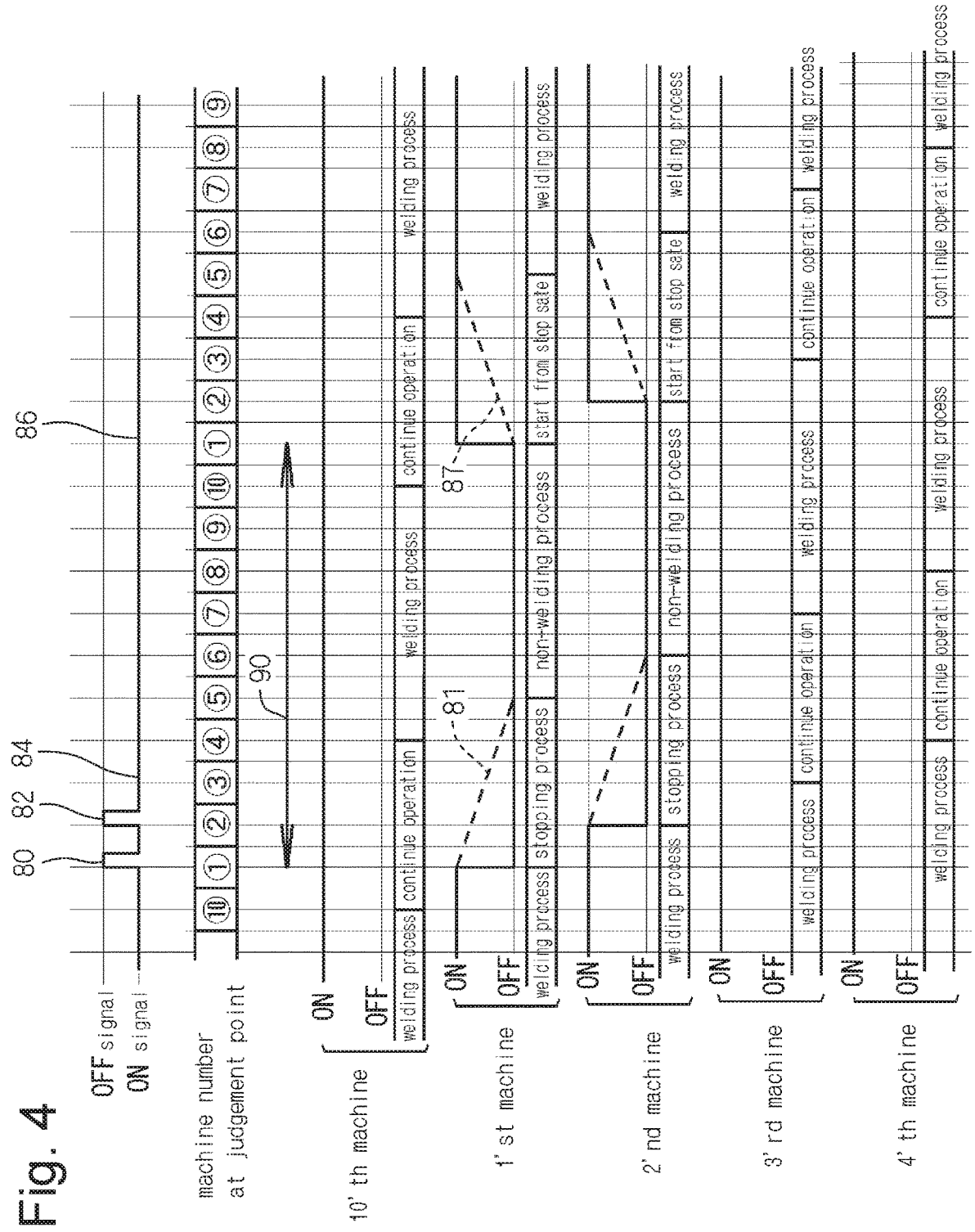

prior art

ULTRASONIC WELDING DEVICE AND ULTRASONIC WELDING METHOD

RELATED APPLICATIONS

The present application is National Phase of International Application No. PCT/JP2017/022591 filed Jun. 19, 2017, and claims priority from Japanese Application No. 2016-137064, filed Jul. 11, 2016, the disclosure of which is hereby incorporated by reference herein in its entirety.

TECHNICAL FIELD

The present invention relates to an ultrasonic welding device and an ultrasonic welding method, more particularly, to an ultrasonic welding device and an ultrasonic welding method for welding a work piece being conveyed by imparting a mechanical vibration thereto.

BACKGROUND ART

The ultrasonic welding device is used, for example, in a disposable diaper manufacturing process.

FIG. 9 is a view conceptually illustrating a disposable diaper manufacturing process. The ultrasonic welding device is used in a welding process (P5) described later.

As shown in FIG. 9, in a conveying process, a belt-shaped work piece W is conveyed continuously in the longitudinal direction thereof. Next, in a leg hole forming process (P2), leg holes L are formed in the work piece W in the longitudinal direction at predetermined intervals. Next, at an absorbent bonding process (P3), an absorbent A is bonded between the leg holes L, L adjacent to each other. Next, in a two-folding process (P4), the work piece W is two-folded and overlapped. Next, in a welding process (P5), welded parts S are formed on the two-folded and overlapped work piece W. It is preferable that the welded parts S, S should be formed simultaneously at two positions adjacent to each other. Next, in a cutting process (P6), the portion between the welded parts S, S adjacent to each other is cut to form individual disposable diapers D.

FIG. 10 is a view showing the outline configuration of an ultrasonic welding device 30x that is used in the welding process (P5). As shown in FIG. 10, the ultrasonic welding device 30x is provided with welding machines 36x disposed at equal intervals around the rotation center axis C1 of a drum 35x. While the two-folded and overlapped work piece W is conveyed along the cylindrical imaginary surface around the drum 35x, the welding machine 36x imparts a mechanical vibration to the work piece W to form the welded parts S. More specifically, the welding machine 36x converts the high-frequency electric signal generated by an oscillator to a mechanical vibration and imparts this mechanical vibration to the work piece W via a horn 9x (for example, refer to Patent Documents 1 and 2).

PRIOR ART DOCUMENT

Patent Document

Patent Document 1: WO 2014/200102
Patent Document 2: WO 2014/200104

SUMMARY OF THE INVENTION

Problem that the Invention is to Solve

The quality of welding is stabilized by using an oscillator that is feedback-controlled so that the amplitude value thereof is not changed depending on a load during the oscillation.

However, if a part to be welded of a work piece has an abnormality, a defect, such as the stoppage of welding, may occur in this kind of oscillator.

For example, if a foreign substance, such as a joint, is present on a web serving as a work piece, the vibration of the horn is hindered by this foreign substance. In this case, feedback control is performed so that the vibration to be imparted to the web becomes constant, whereby the power to be supplied to the oscillator is increased. When the power to be supplied to the oscillator becomes excessive, the operation of the oscillator stops abnormally. Recovery thereafter is not easy, and welding is stopped until the recovery is completed. In some cases, the oscillator is broken.

In consideration of these circumstances, the present invention is intended to provide an ultrasonic welding device and an ultrasonic welding method capable of avoiding a defect resulting from welding a part to be welded of a work piece in which there is an abnormality.

Means for Solving the Problem

The present invention provides an ultrasonic welding device having been configured as described below in order to solve the above-mentioned problem.

The ultrasonic welding device is provided with: (a) a support device configured so as to support a work piece along a predetermined conveyance surface; (b) a welding machine including an oscillator for generating a high-frequency electric signal, a transducer for converting the high-frequency electric signal to a mechanical vibration, and a horn to which the mechanical vibration is transmitted, the horn being disposed so as to face a part to be welded of the work piece supported along the conveyance surface, and the mechanical vibration being imparted via the horn to the part to be welded, whereby the part to be welded is welded; (c) a detector for detecting an abnormality in the part to be welded of the work piece, the detector being disposed further upstream in the conveyance direction of the work piece than the support device; and (d) a protective device for prohibiting the welding machine from welding the part to be welded of the work piece in which the abnormality is detected by the detector.

With the above-mentioned configuration, since the part to be welded of the work piece in which the abnormality is detected is not welded, it is possible to avoid a defect resulting from welding the part to be welded of the work piece in which the abnormality is detected.

The protective device preferably includes a controller for stopping the oscillator of the welding machine at the time when the horn of the welding machine faces the part to be welded of the work piece in which the abnormality is detected by the detector.

In this case, since the oscillator of the welding machine is stopped, the oscillator is not feedback-controlled for the part to be welded of the work piece in which the abnormality is detected, whereby the power to be supplied to the oscillator does not become excessive.

The welding machine preferably includes an anvil disposed so as to face the horn and a contacting/separating mechanism for moving at least either one of the horn and the anvil in a direction away from the other. The protective device includes a controller for controlling the contacting/separating mechanism so that at least either one of the horn and the anvil is moved in the direction away from the other at the time when the horn of the welding machine faces the part to be welded of the work piece in which the abnormality is detected by the detector.

In this case, for the part to be welded of the work piece in which the abnormality is detected, since the vibration of the horn is not hindered, a situation does not occur in which feedback control is performed so that the vibration to be imparted to the web becomes constant and the power to be supplied to the oscillator becomes excessive.

The ultrasonic welding device is preferably provided with a plurality of welding machines.

Since it takes time to stop and restart the operation of the welding machine by using the protective device, in the case that a plurality of welding machines is provided, while a certain welding machine is stopped or restarted, the part to be welded of the work piece can be welded using another welding machine, whereby the conveyance speed and the processing efficiency of the work piece can be raised.

The support device is preferably a drum having work piece support members disposed along the cylindrical imaginary surface thereof. A portion of the imaginary surface serves as the conveyance surface.

Although the conveyance surface can be set to an arbitrary shape, such as a linear shape or a U shape, in the case that the conveyance surface is cylindrical, the horn of the welding machine is easily disposed so as to face the part to be welded of the work piece that is supported along the conveyance surface.

Furthermore, the present invention provides an ultrasonic welding method configured as described below to solve the above-mentioned problem.

The ultrasonic welding method is provided with (i) a conveying process for conveying a work piece while supporting the work piece along a conveyance surface and for disposing a part to be welded of the work piece between a horn and an anvil; (ii) a welding process for holding the part to be welded of the work piece between the horn and the anvil and for imparting the mechanical vibration that is converted from the electric signal generated by an oscillator to the part to be welded via the horn, thereby welding the part to be welded; (iii) a detecting process for detecting an abnormality of the part to be welded of the work piece at a position further upstream in the conveyance direction of the work piece than the horn and the anvil; and (iv) a protecting process for prohibiting the welding of the part to be welded of the work piece in which the abnormality is detected.

With the above-mentioned method, since the part to be welded of the work piece in which the abnormality is detected is not welded, it is possible to avoid a defect resulting from welding the part to be welded of the work piece in which the abnormality is detected.

The protecting process preferably stops the oscillator when the part to be welded of the work piece in which the abnormality is detected is disposed between the horn and the anvil.

In this case, since the oscillator of the welding machine is stopped for the part to be welded of the work piece in which the abnormality is detected, the oscillator is not feedback-controlled, whereby the power to be supplied to the oscillator does not become excessive.

When the part to be welded of the work piece in which the abnormality is detected is disposed between the horn and the anvil, the protecting process preferably prevents the part to be welded from being held between the horn and the anvil by moving at least either one of the horn and the anvil in a direction away from the other.

In this case, for the part to be welded of the work piece in which the abnormality is detected, since the vibration of the horn is not hindered, a situation does not occur in which feedback control is performed so that the vibration to be imparted to the web becomes constant and the power to be supplied to the oscillator becomes excessive.

Plural sets, each being composed of the horn, the anvil and the oscillator, are preferably provided.

Since it takes time to stop and restart the mechanical vibration of the horn, in the case that the plural sets, each being composed of the horn and so on, are provided, while the mechanical vibration of the horn in a certain set is stopped or restarted, the part to be welded of the work piece can be welded using the horn in another set, whereby the conveyance speed and the processing efficiency of the work piece can be raised.

In the welding process, the conveyance surface is a portion of the cylindrical imaginary surface.

In the welding process, although the conveyance surface can be set to an arbitrary shape, such as a linear shape or a U shape, in the case that the conveyance surface is a portion of the cylindrical imaginary surface, the part to be welded of the work piece is held between the horn and the anvil and welded easily.

Advantage of the Invention

With the present invention, it is possible to avoid a defect resulting from welding a part to be welded of a work piece in which there is an abnormality.

BRIEF DESCRIPTION OF THE DRAWINGS

FIG. 4 is a timing chart of the ultrasonic welding device (Embodiment 1);

MODE FOR CARRYING OUT THE INVENTION

Embodiments according to the present invention will be described below referred to the drawings. An ultrasonic welding device according to the present invention can be built, for example, in a disposable diaper manufacturing line and used.

Embodiment 1

An ultrasonic welding device 30 according to Embodiment 1 will be described referring to FIGS. 1 to 4.

Figure 1:
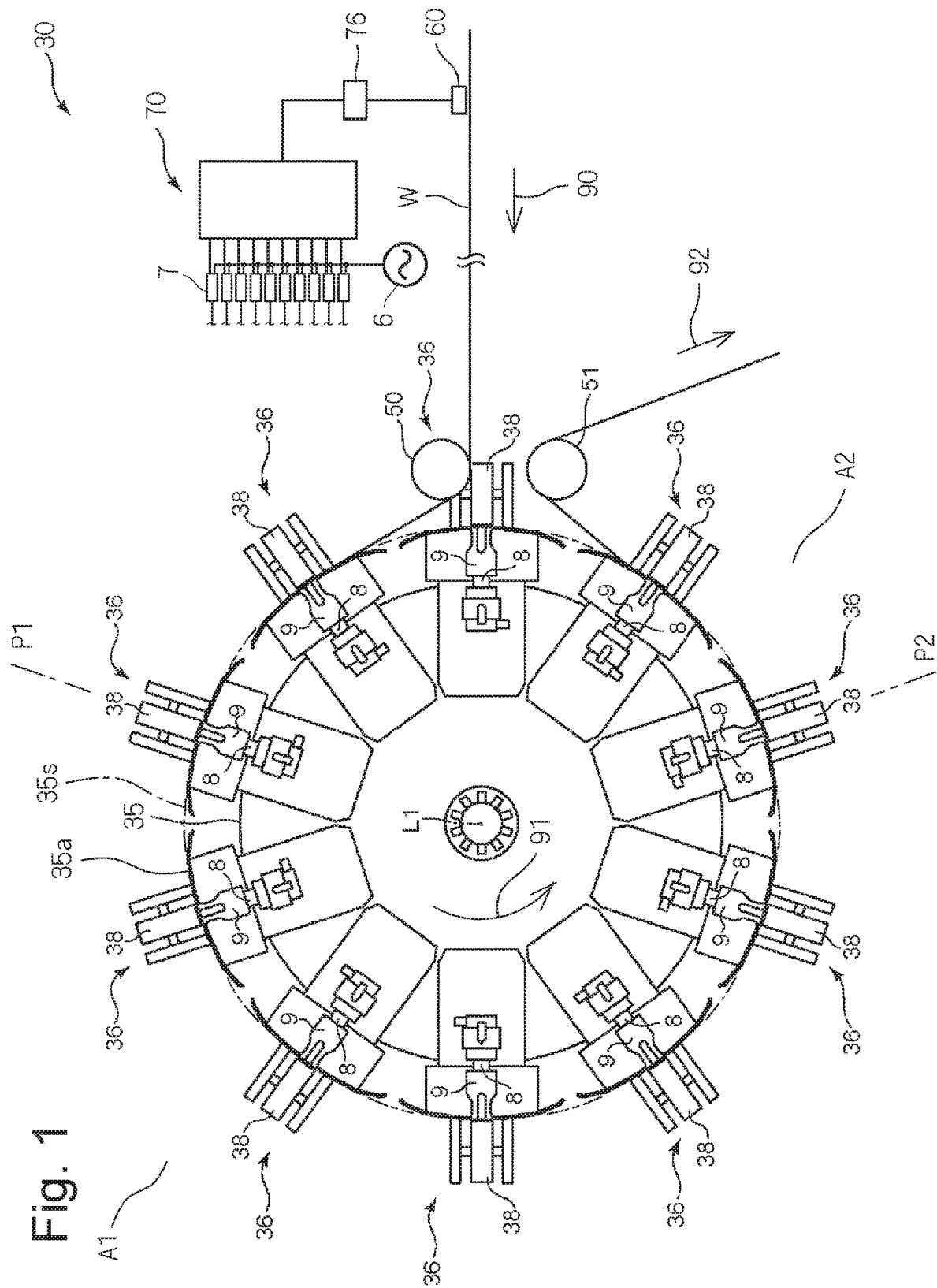
FIG. 1 is a view showing the configuration of an ultrasonic welding device (Embodiment 1)
Figure 2:
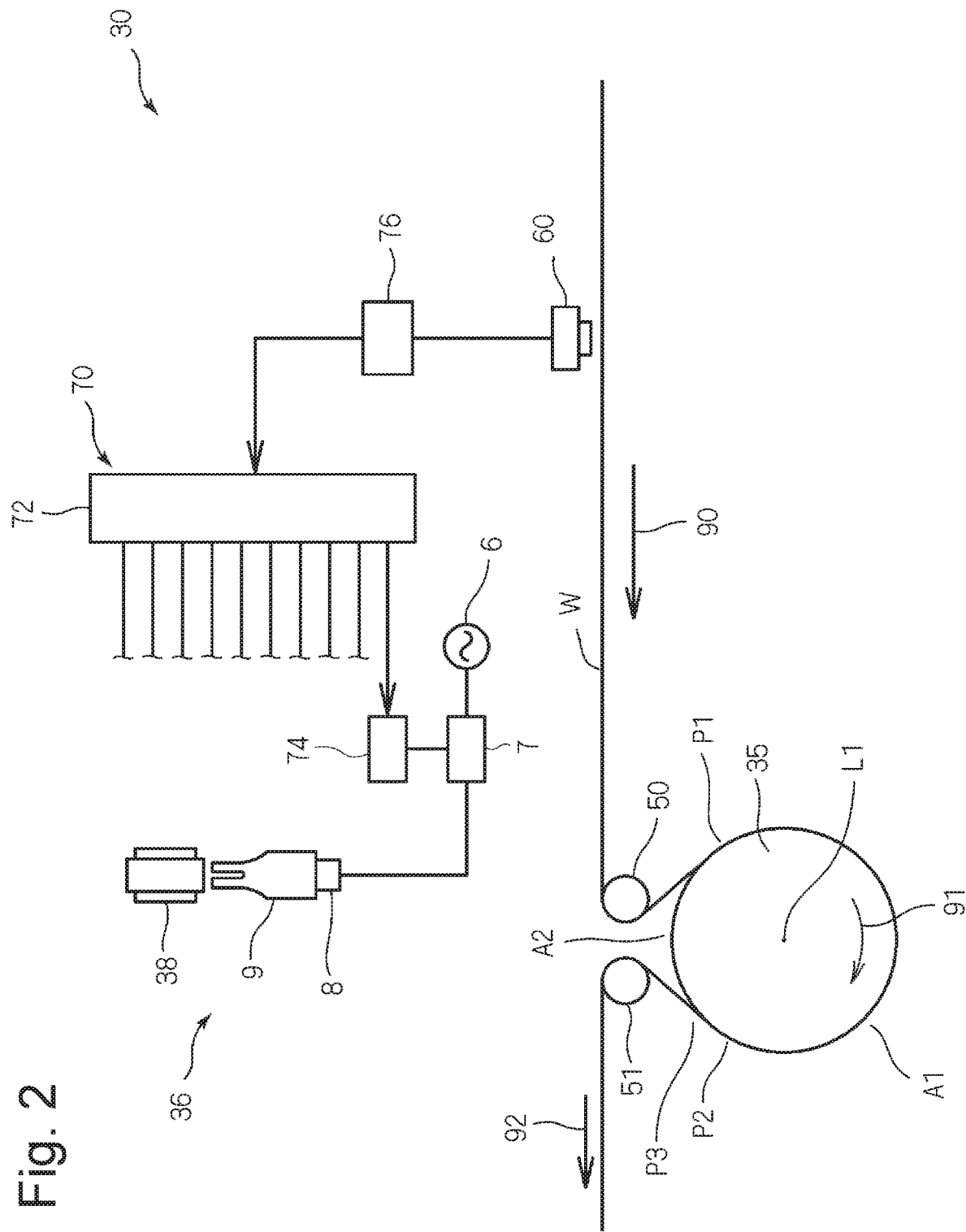
FIG. 2 is a block diagram showing the ultrasonic welding device (Embodiment 1)

FIG. 1 is a view showing the configuration of the ultrasonic welding device 30. FIG. 2 is a block diagram conceptually showing the configuration of the ultrasonic welding device 30. As shown in FIGS. 1 and 2, in the ultrasonic welding device 30, one or two or more (10 in FIG. 1) welding machines 36 (not shown in FIG. 2) are disposed around a drum 35, and the welding machines 36 are moved around the drum 35 in synchronization with the rotation of the drum 35. An introducing roller 50 and a discharging roller 51 are provided adjacent to the drum 35. The ultrasonic welding device 30 is further provided with a detector 60 and a protective device 70. A work piece W is conveyed in the direction indicated by arrows 90 and 92, and passes through the detector 60, the introducing roller 50, the drum 35 and the discharging roller 51. The drum 35 is rotated in the direction indicated by an arrow 91 in synchronization with the conveyance of the work piece W. The work piece W may be a continuous body or may be formed of individual pieces. For example, the work piece may be a web to be supplied continuously or may be formed of individual pieces to be supplied intermittently.

As shown in FIG. 1, the drum 35 is configured so to support the work piece W along the cylindrical imaginary surface 35s thereof that is concentric with the rotation center axis L1 of the drum 35. In other words, the drum 35 has a plurality of work piece support members 35a disposed mutually at intervals along the imaginary surface 35s. The work piece W is disposed on the outside of the work piece support members 35a, that is, on the opposite side of the rotation center axis L1, and is supported by the work piece support members 35a. A portion of the imaginary surface 35s, that is, the portion of the imaginary surface 35s for supporting the work piece W serves as the conveying surface of the present invention. The drum 35 serves as the support device of the present invention.

The work piece W may be suction-held by vacuuming the space inside from the work piece support members 35a, that is, on the side of the rotation center axis L1.

The welding machine 36 is disposed so as to cross the imaginary surface 35s as viewed from the direction parallel to the rotation center axis L1. In other words, in the welding machine 36, a transducer 8 and a horn 9 are disposed inside from the imaginary surface 35s, that is, on the side of the rotation center axis L1, and an anvil 38 is disposed outside from the imaginary surface 35s, that is, on the opposite side of the rotation center axis L1.

To the protective device 70, an oscillator 7 (not shown in FIG. 1, see FIG. 2) is connected for each welding machine 36. Each oscillator 7 is connected to a power source 6 (see FIG. 2) and generates a high-frequency electric signal. The transducer 8 is connected to the oscillator 7 and converts the high-frequency electric signal generated by the oscillator 7 to a mechanical vibration. The mechanical vibration converted by the transducer 8 is transmitted to the horn 9. An amplifier for amplifying the mechanical vibration may or may not be provided between the transducer 8 and the horn 9. The horn 9 is disposed so that the tip end thereof on the opposite side of the transducer 8 is exposed from the work piece support members 35a and faces a part to be welded of the work piece W that is supported along the imaginary surface 35s. The transducer 8 and the horn 9 are fixed to the drum 35 and are integrally rotated with the drum 35.

The anvil 38 is disposed so as to face the horn 9 as viewed from the direction parallel to the rotation center axis L1. The anvil 38 is fixed to the drum 35 so as to be movable in the direction parallel to the rotation center axis L1. The anvil 38 is moved with the rotation of the drum 35 while keeping the relative position between the anvil 38 and the drum 35 in the circumferential direction of the drum 35.

While the welding machine 36 is moved in the welding area A1 ranging from a welding start position P1 to a welding stop position P2, the anvil 38 is brought into a state in which the anvil 38 faces the horn 9 and the work piece W is held between the anvil 38 and the horn 9. At this time, the mechanical vibration is imparted to the part to be welded of the work piece W via the horn 9, whereby the part to be welded of the work piece W is welded and a welded part is formed. For example, the welded part is formed on the two-folded continuous body of a work piece.

While the welding machine 36 is moved in the non-welding area A2 ranging from the welding stop position P2 to the welding start position P1, the anvil 38 is moved in the direction parallel to the rotation center axis L1 to avoid interference with portions other than the portion of the work piece W supported along the imaginary surface 35s and also to avoid interference with the introducing roller 50 and the discharging roller 51.

The horn 9 and so on may be disposed outside from the imaginary surface 35s (on the opposite side of the rotation center axis L1) and the anvil 38 may be disposed inside from the imaginary surface 35s (on the side of the rotation center axis L1). Furthermore, like the anvil 38, the horn 9 and so on may be configured so as to be movable in the direction parallel to the rotation center axis L1.

The detector 60 is disposed further upstream in the conveyance direction of the work piece W than the drum 35. The detector 60 is, for example, an image sensor or a thickness sensor, and detects an abnormality in the part to be welded of the work piece W. For example in the case that the work piece W is a continuous body, the detector detects an abnormality, such as the presence of a foreign substance on a joint of the continuous body or an abnormal thickness of a joint of the continuous body.

The protective device 70 is a control device for prohibiting the welding machine 36 from welding the part to be welded of the work piece in which an abnormality is detected by the detector 60.

As shown in FIG. 2, the protective device 70 has a control section 72, a controller 74 provided for each welding machine 36, and a PLC 76. In FIG. 2, one controller 74 and one welding machine 36 are shown, and the other controllers and the other welding machines are not shown.

The control section 72 is a computer that operates according to a predetermined program, and the PLC 76 connected to the detector 60 and the respective controllers 74 are connected thereto.

A detection signal is input from the detector 60 to the PLC 76, and the PLC 76 outputs an instruction signal to the control section 72. The PLC 76 is a sequencer that operates according to a predetermined program. The PLC 76 includes a memory or the like to temporarily store information indicating an abnormality in the part to be welded of the work piece detected by the detector 60. When the part to be welded of the work piece W in which the abnormality is detected has reached a predetermined position further upstream than the drum 35 of the ultrasonic welding device 30, the PLC 76 outputs the reach information as an instruction signal to the control section 72.

When the instruction signal is input to the control section 72 from the PLC 76, the control section 72 selects the welding machine 36 corresponding to the part to be welded of the work piece in which the abnormality is detected and transmits the instruction signal to the controller 74 corresponding to the welding machine 36.

The controller 74 is a driver connected to the oscillator 7 of the welding machine 36. The controller 74 transmits control signals for controlling the start and stop of the oscillator 7 to the oscillator 7 according to the instruction signal from the control section 72.

The part to be welded of the work piece W is disposed between the horn 9 and the anvil 38 of the welding machine sequentially at a predetermined speed and a predetermined timing. The control section 72 predicts the welding machine 36 wherein the part to be welded of the work piece in which the abnormality is detected is disposed between the horn 9 and the anvil 38 thereof and also predicts the time when the part to be welded is disposed therebetween, and the control section 72 prohibits the welding machine 36 from welding the part to be welded of the work piece W in which the abnormality is detected at the time when the part to be welded of the work piece in which the abnormality is detected is disposed between the horn 9 and the anvil 38.

More specifically, when the welding machine 36 reaches a judgment point P3 further downstream than the welding stop position P2, the control section 72 transmits an instruction signal to the controller 74 on the basis of the presence/absence of abnormality detection for the part to be welded of the work piece that is to be welded next by the welding machine 36. On the basis of the instruction signal, the controller 74 transmits a control signal to the oscillator 7 of the welding machine 36 while the welding machine 36 is in the non-welding area A2, thereby stopping or restarting the oscillator 7 or continuing the operation state after the start.

Although the transducer 8 and the horn 9 are switched to the stop state or the start state by stopping or starting the oscillator 7, since a certain time, for example, appropriately 100 to 200 ms, is required for the switching of the state, the time required for the movement of the welding machine 36 from the judgment point P3 to the welding start position P1 is set longer than the time required for the switching of the state of the transducer 8 and the horn 9.

Figure 3:
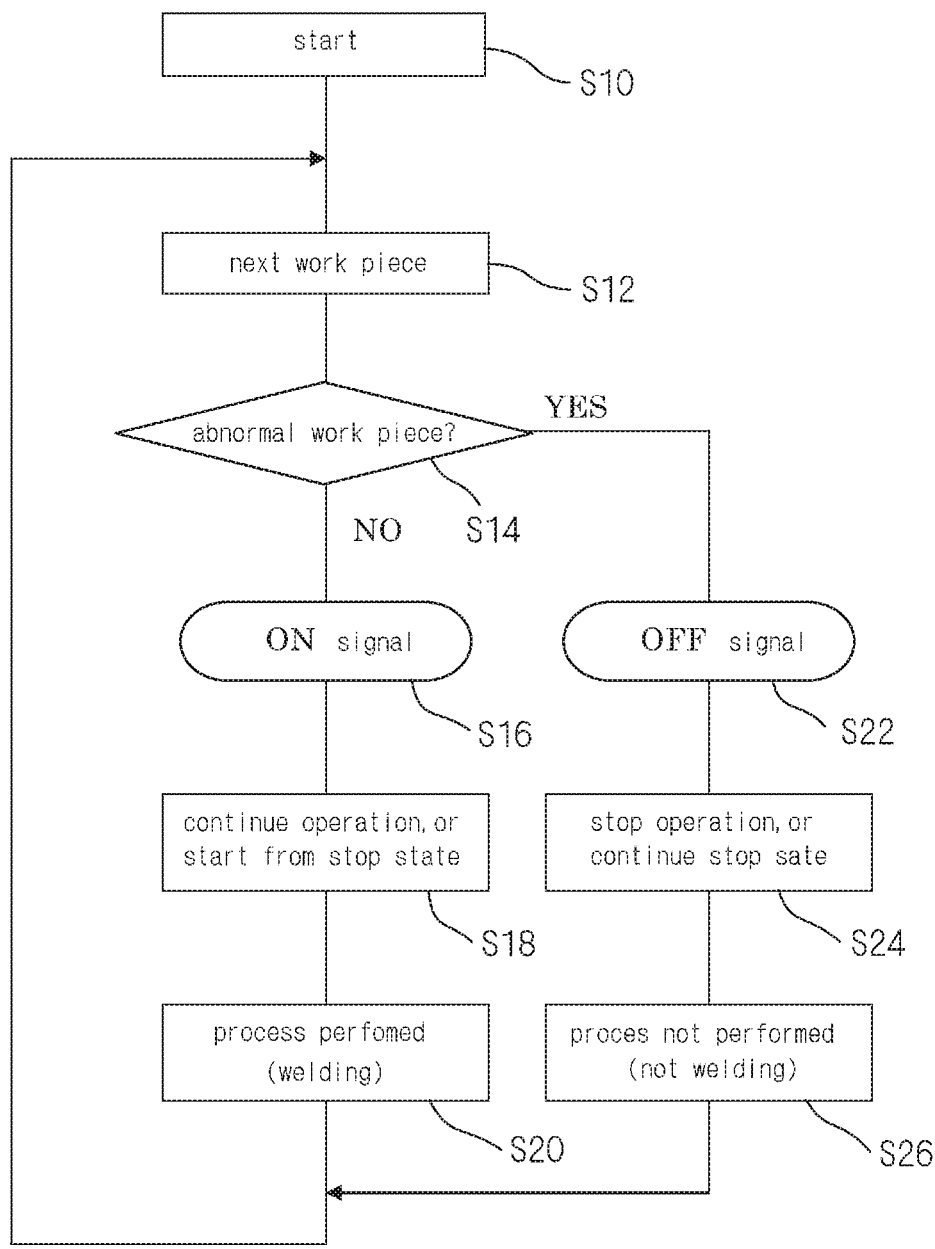
FIG. 3 is a flow chart of the ultrasonic welding device (Embodiment 1)

FIG. 3 is a flow chart of the operation of the ultrasonic welding device 30. As shown in FIG. 3, when the protective device 70 is started (at S10), the presence/absence of abnormality detection is confirmed for the part to be welded of the work piece that is to be welded next by the welding machine having reached the judgment point, for example, by reading information from the memory (at S12).

If no abnormality is detected in the part to be welded of the work piece that is to be welded next by the welding machine (NO at S14), the control signal for turning ON the oscillator of the welding machine is transmitted from the controller to the oscillator (at S16), and the oscillator of the welding machine continues the operation state after the start or starts from the stop state (at S18). Next, when the welding machine passes through the welding area, a welding process for welding the part to be welded of the work piece that is to be welded next and in which no abnormality is detected is performed (at S20), and the procedure returns to step S12.

If an abnormality is detected in the part to be welded of the work piece that is to be welded next by the welding machine (YES at S14), the control signal for turning OFF the oscillator of the welding machine is transmitted from the controller to the oscillator (at S22), and the oscillator of the welding machine stops operation or continues the stop state (at S24). Next, when the welding machine passes through the welding area, the part to be welded of the work piece that is to be welded next and in which the abnormality is detected is not welded (at S26), and the procedure returns to step S12.

FIG. 4 is a timing chart showing an example of the operation of the ultrasonic welding device 30. The first to tenth welding machines sequentially pass through the judgment point, and when each welding machine passes through the judgment point, the control signal for turning ON or OFF the oscillator is transmitted to the oscillator.

The one cycle indicated by an arrow 90 in FIG. 4 will be described. For example, in the first and second machines, in the case that the part to be welded of the work piece that is to be welded next has an abnormality, when the first machine passes through the judgment point, the controller of the protective device outputs a control signal 80 for turning OFF the oscillator to the oscillator of the first machine. Next, when the second machine passes through the judgment point, the controller of the protective device outputs a control signal 82 for turning OFF the oscillator to the oscillator of the second machine. Next, when the third machine passes through the judgment point, the controller of the protective device outputs a control signal 84 for turning ON the oscillator to the oscillator of the third machine. Hereafter, when each of the third to tenth welding machines passes through the judgment point, the controller of the protective device outputs a control signal for turning ON the oscillator to the oscillator of the welding machine having passed through the judgment point.

The first machine having received the control signal 80 for turning OFF the oscillator enters the non-welding area A2, and the transducer 8 and the horn 9 are switched to the stop state as indicated by a broken line 81 while the first machine is in the non-welding area A2. Next, since the oscillator is OFF and the transducer 8 and the horn 9 have been switched to the stop state while the first machine is in the welding area, the first machine does not weld the part to be welded of the work piece that is to be welded next. When the first machine passes through the judgment point again, the controller of the protective device outputs a control signal 86 for turning ON the oscillator to the oscillator of the first machine. Hence, while the first machine is in the non-welding area, the transducer 8 and the horn 9 are restarted and switched to the start state as indicated by a broken line 87. Next, the first machine enters the welding area, and since the oscillator is ON and the transducer 8 and the horn 9 are switched to the start state while the first machine is in the welding area, the first machine performs a welding process. The second machine operates similarly with the first machine.

In each of the third and following machines, while the machine is in the non-welding area, the oscillator keeps the ON state, and then the machine enters the welding area, while the machine is in the welding area, since the oscillator keeps the ON state, a welding process is performed.

Next, the operation of the ultrasonic welding device 30 will be described.

The drum 35 of the ultrasonic welding device 30 is rotated in synchronization with the conveyance of the work piece W. At this time, the drum 35 conveys the work piece W while supporting the work piece W along the cylindrical imaginary surface 35s around the drum 35 and disposes the part to be welded of the work piece W between the horn 9 and the anvil 38. This is a conveying process.

The welding machine 36 of the ultrasonic welding device 30 holds the part to be welded of the work piece W to be conveyed along the imaginary surface 35s between the horn 9 and the anvil 38 and imparts the mechanical vibration that is converted from the electric signal generated by the oscillator 7 to the part to be welded via the horn 9, thereby welding the part to be welded. This is a welding process.

The detector 60 of the ultrasonic welding device 30 detects an abnormality of the part to be welded of the work piece W at a position further upstream in the conveyance direction of the work piece W than the drum 35. This is a detecting process.

The protective device 70 of the ultrasonic welding device 30 prohibits the welding machine 36 from welding the part to be welded of the work piece W in which an abnormality is detected. This is a protecting process.

In the case that the work piece is formed of individual pieces, the work piece including a part to be welded in which an abnormality is detected and which is prohibited from being welded is removed from the conveyance route for normal work pieces in the processes subsequent to the protection process. In the case that the work piece is a continuous body including a plurality of parts to be welded, in the processes subsequent to the protecting process, the work piece is divided into individual pieces and the individual pieces including the parts to be welded in which abnormalities are detected and which are prohibited from being welded are removed from the conveyance route for normal individual pieces.

As described above, during the standby period in which the welding machine 36 is in the non-welding area A2, the oscillator 7 of the welding machine 36 is turned ON/OFF, whereby only the part to be welded of the work piece W in which an abnormality is detected is not welded and the other normal parts to be welded of the work piece W can be welded.

Since the oscillator 7 of the welding machine 36 is stopped for the part to be welded of the work piece W in which the abnormality is detected, the oscillator 7 is not feedback-controlled, whereby the power to be supplied to the oscillator 7 does not become excessive.

Since it takes time to stop and restart the mechanical vibration of the horn 9, in the case that a plurality of welding machines 36 is provided and a plurality of horns 9 is used, while the mechanical vibration of the horn 9 of a certain welding machine 36 is stopped or restarted, the part to be welded of the work piece W can be welded using the horn 9 of another welding machine 36, whereby the conveyance speed and the processing efficiency of the work piece W can be raised. Furthermore, with the plurality of horns 9, the work piece waiting time for the work piece assigned for each horn 9 can be extended; hence, even in the case that the conveyance speed of the work piece W is increased, it is preferable that the state can be switched easily. In other words, in the case that n pieces of the horns 9 are provided, each one of every n pieces of the horns 9 may merely process the work piece W, whereby the work piece waiting time can be extended. Hence, it is preferable that the ultrasonic welding device 30 should be provided with a plurality of welding machines 36.

As described above, when the part to be welded of the work piece W has an abnormality, the ultrasonic welding device 30 stops the welding machine 36, whereby it is possible to avoid a defect resulting from welding the part to be welded of the work piece in which there is the abnormality.

Embodiment 2

An ultrasonic welding device 30*a* according to Embodiment 2 will be described referring to FIGS. 5 and 6. In the ultrasonic welding device 30*a* according to Embodiment 2, in the case that the part to be welded of the work piece W has an abnormality, welding is prevented by making the distance between the anvil 38 and the horn 9 larger, instead of stopping the oscillator 7 of the welding machine 36. In the following description, the same components as those in Embodiment 1 are designated by the same numerals and signs, and differences from Embodiment 1 will be mainly described.

Figure 5A:
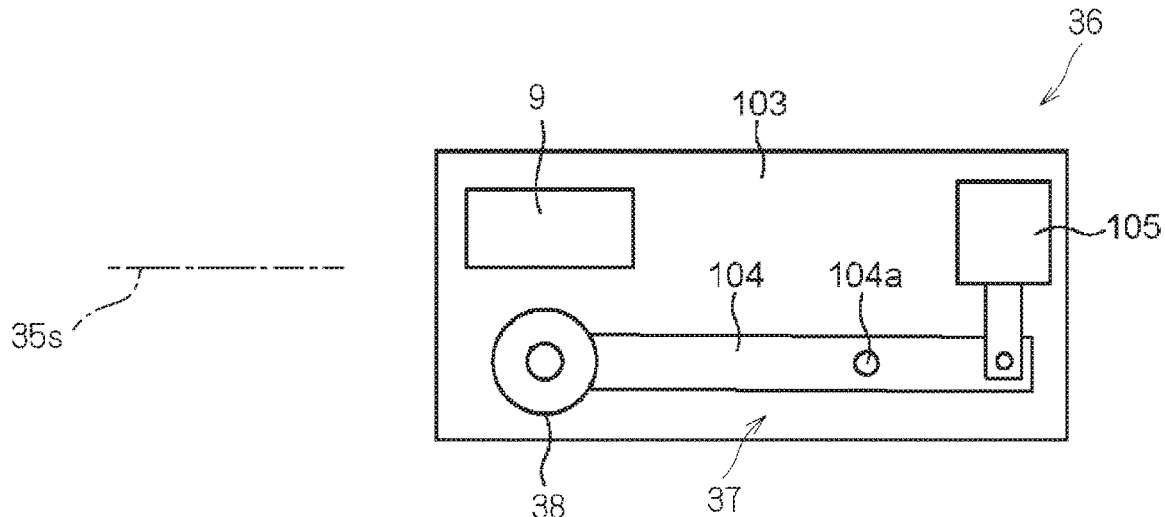
FIGS. 5(a), 5(b) and 5(c) are views showing the configuration of the main sections of an ultrasonic welding device (Embodiment 2)
Figure 5B:
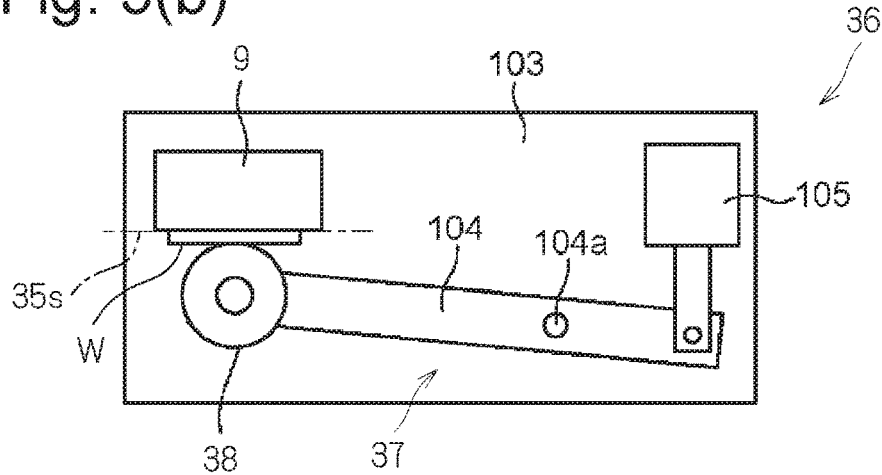
Figure 5C:
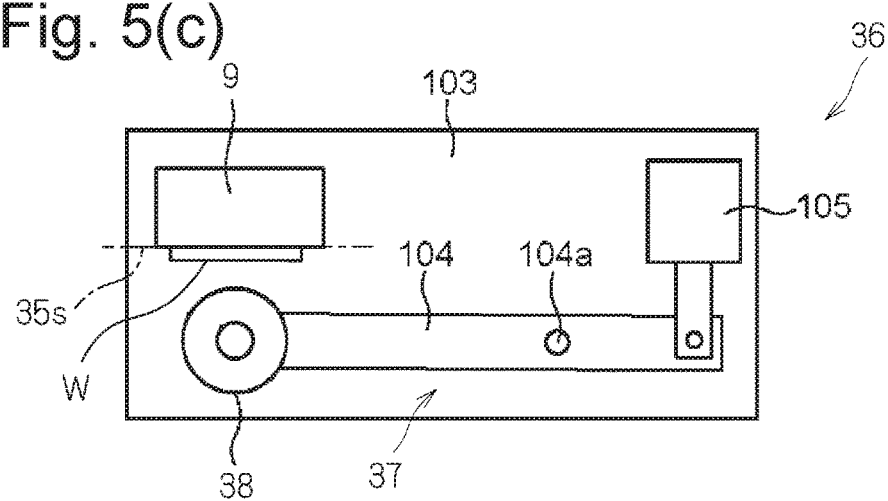

FIG. 5 is a view showing the configuration of the main sections of the ultrasonic welding device 30*a* according to Embodiment 2. As shown in FIG. 5, the welding machine 36 includes a contacting/separating mechanism 37 for moving the anvil 38 in a direction away from the horn 9. The contacting/separating mechanism 37 includes a cylinder 105 and a lever 104.

More specifically, the transducer 8 (not shown in FIG. 5, see FIG. 6), the horn 9, the cylinder 105 and a lever support shaft 104*a* are fixed to a support member 103.

The lever support shaft 104*a* rotatably supports the intermediate portion of the lever 104. One end section of the lever 104 is link-connected to the operation shaft of the cylinder 105. At the other end section of the lever 104, the anvil 38 is rotatably supported.

Figure 6:
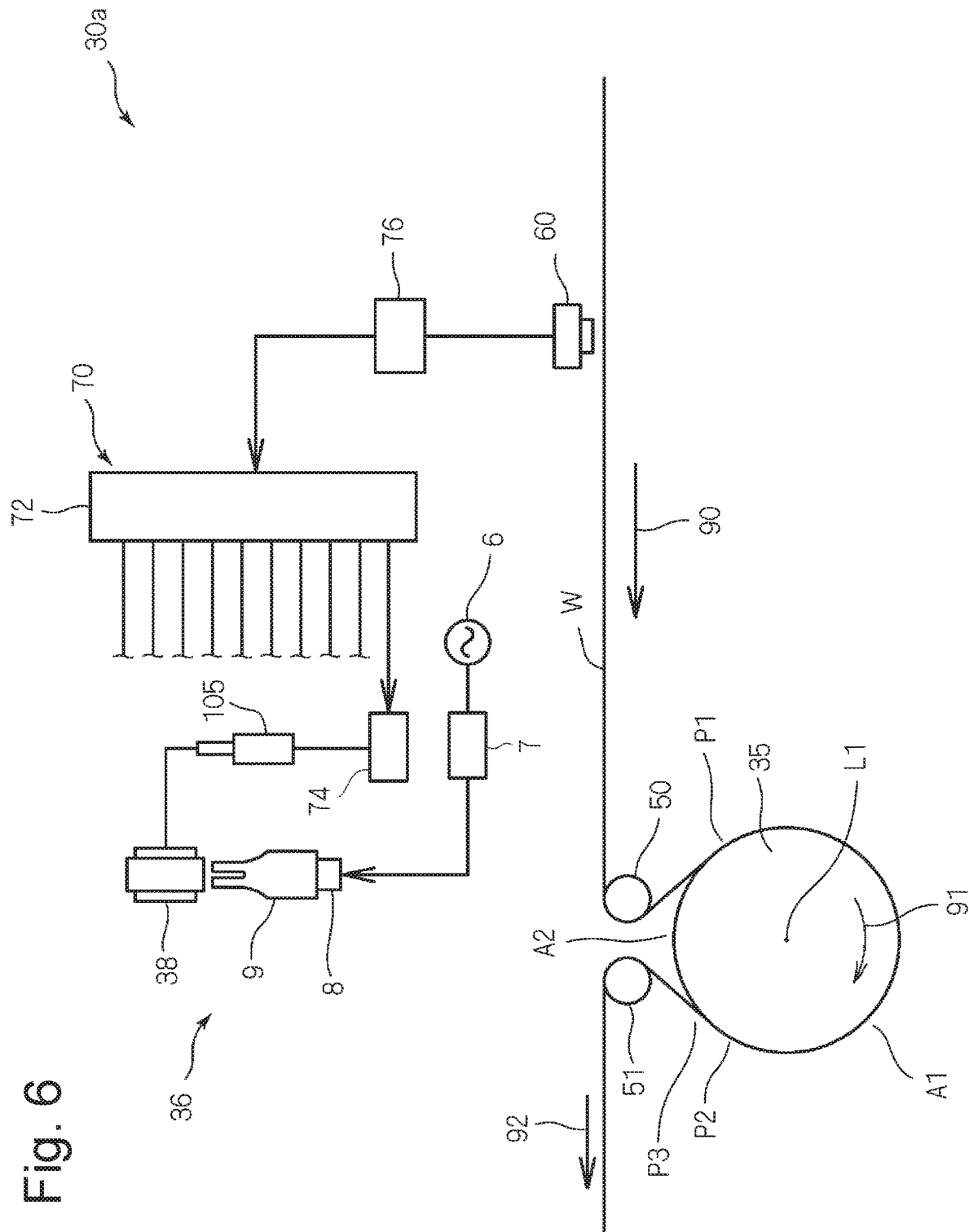
FIG. 6 is a block diagram of the ultrasonic welding device (Embodiment 2)

FIG. 6 is a block diagram conceptually showing the configuration of the ultrasonic welding device 30*a* according to Embodiment 2. As shown in FIG. 6, the controller 74 of the protective device 70 is connected to the cylinder 105 of the contacting/separating mechanism 37. The protective device 70 controls the extension and retraction of the cylinder 105 of the contacting/separating mechanism 37 via the controller 74.

When the welding machine 36 is in the welding area A1, the cylinder 105 usually extends as shown in FIG. 5(*b*), and the anvil 38 is moved toward the horn 9, whereby the part to be welded of the work piece W supported along the imaginary surface 35*s* of the drum 35 is held between the horn 9 and the anvil 38 and then welded.

When the welding machine 36 is in the non-welding area A2, the cylinder 105 retracts as shown in FIG. 5(*a*), the anvil 38 is moved in the direction away from the horn 9, and the support member 103 is moved in the direction parallel to the rotation center axis L1 of the drum 35. At this time, the anvil 38 and the horn 9 are away from the position facing the imaginary surface 35*s*.

The operation of the ultrasonic welding device 30*a* is the same as the operation of the ultrasonic welding device 30 according to Embodiment 1, except for the protecting process. In the protecting process, the ultrasonic welding device 30*a* operates as described below.

When the part to be welded of the work piece W in which an abnormality is detected is disposed between the horn 9 and the anvil 38, the protective device 70 controls the cylinder 105 via the controller 74 so that the anvil 38 is moved in the direction away from the horn 9 as shown in FIG. 5(*c*). In other words, the anvil 38 is moved in the direction away from the horn 9 so that the part to be welded of the work piece W is not held between the horn 9 and the anvil 38. Hence, the part to be welded of the work piece W in which the abnormality is detected is not welded. That is to say, welding is prohibited.

For the part to be welded of the work piece W in which the abnormality is detected, since the vibration of the horn is not hindered, a situation does not occur in which feedback control is performed so that the vibration to be imparted to the web becomes constant and the power to be supplied to the oscillator becomes excessive. Hence, it is possible to avoid a defect resulting from welding the part to be welded of the work piece in which there is the abnormality.

However, instead of moving the anvil 38 in the direction away from the horn 9, the horn 9 may be moved in a direction away from the anvil 38 or both the horn 9 and the anvil 38 may be moved in the directions away from each other.

Embodiment 3

An ultrasonic welding device 30b according to Embodiment 3 additionally provided with two endless belts 40 and 42 will be described referring to FIGS. 7 and 8.

Figure 7:
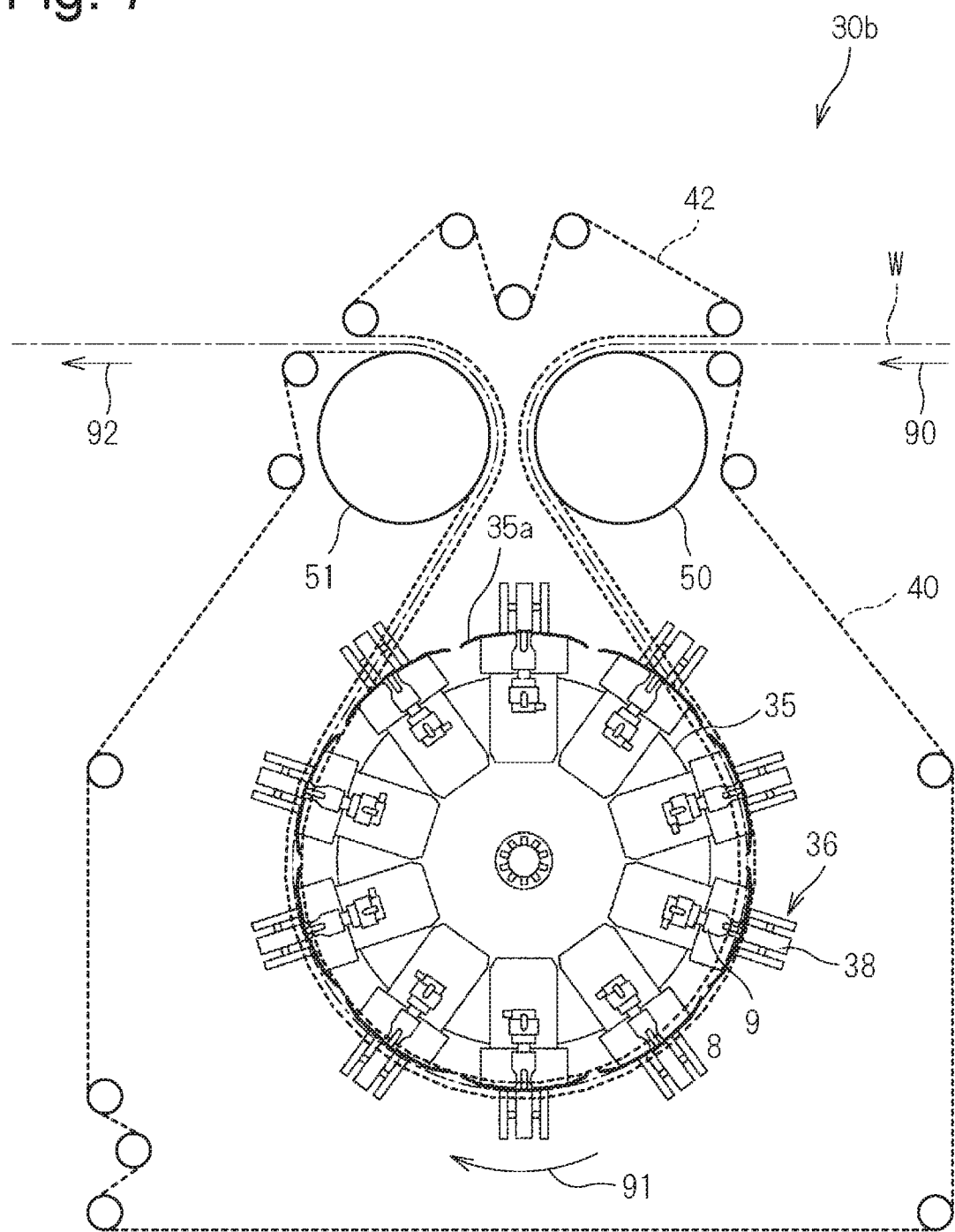
FIG. 7 is a view showing the configuration of an ultrasonic welding device (Embodiment 3)

FIG. 7 is a view conceptually showing the configuration of the ultrasonic welding device 30b according to Embodiment 3. As shown in FIG. 7, the ultrasonic welding device 30b is configured similarly to the welding devices according to Embodiments 1 and 2, except for the configuration in which the two endless belts 40 and 42 are circulated. In other words, as in Embodiments 1 and 2, the welding machines 36 are disposed around the drum 35, and the introducing roller 50 and the discharging roller 51 are provided adjacent to the drum 35. The work piece W indicated by a chain line is conveyed in the directions indicated by arrows 90 and 92 in synchronization with the rotation of the drum 35 indicated by an arrow 91.

The ultrasonic welding device 30b is configured so that the two endless belts 40 and 42 indicated by broken lines are disposed on both the sides of the conveyance route of the work piece W along the conveyance route of the work piece W and circulate.

Figure 8:
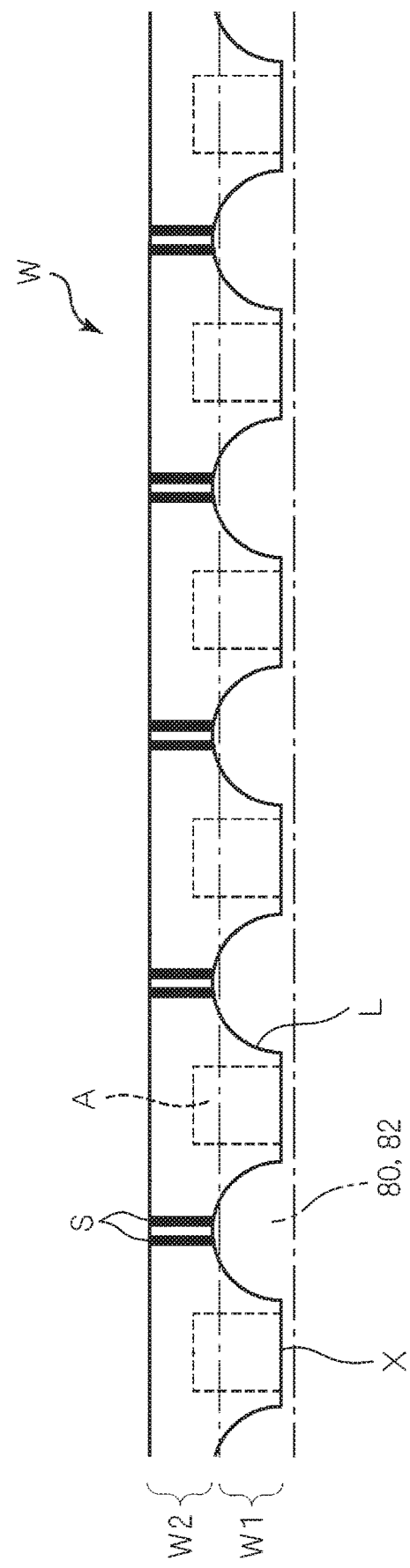
FIG. 8 is a view illustrating a work piece (Embodiment 3)
Figure 9:
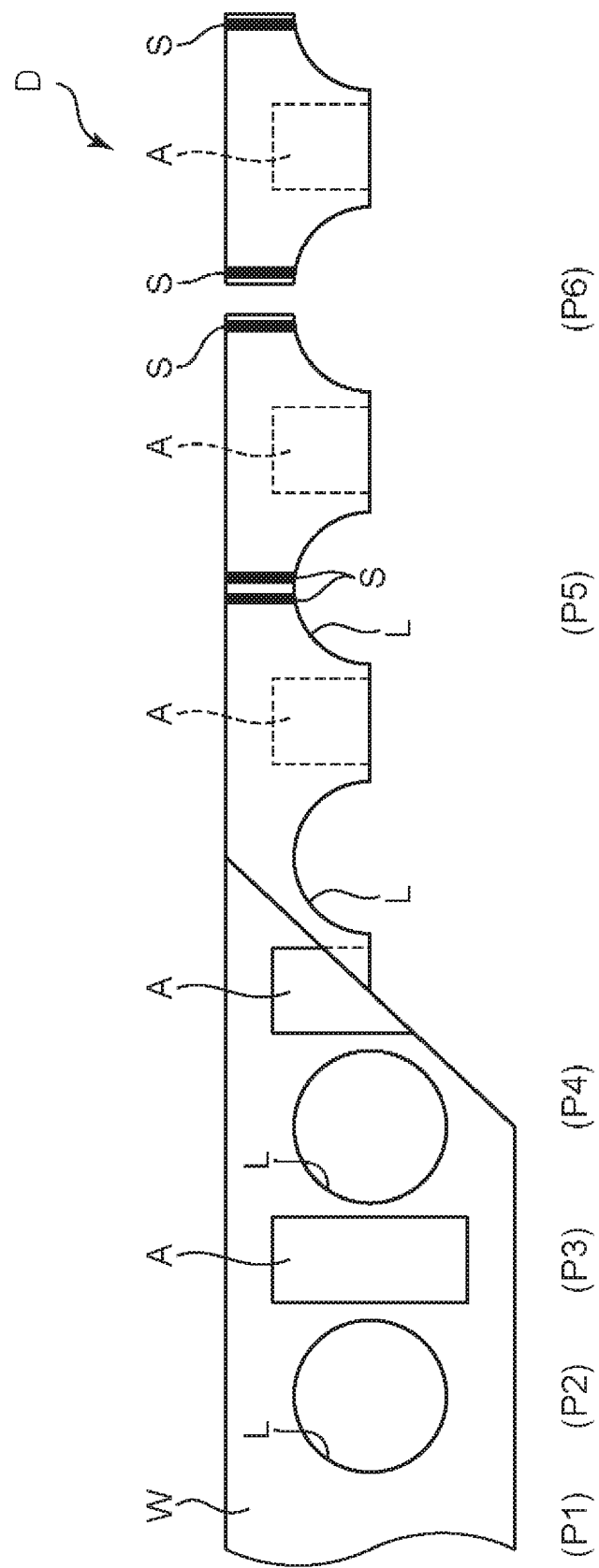
FIG. 9 is a view illustrating a disposable diaper manufacturing process (Conventional example 1)
Figure 10:
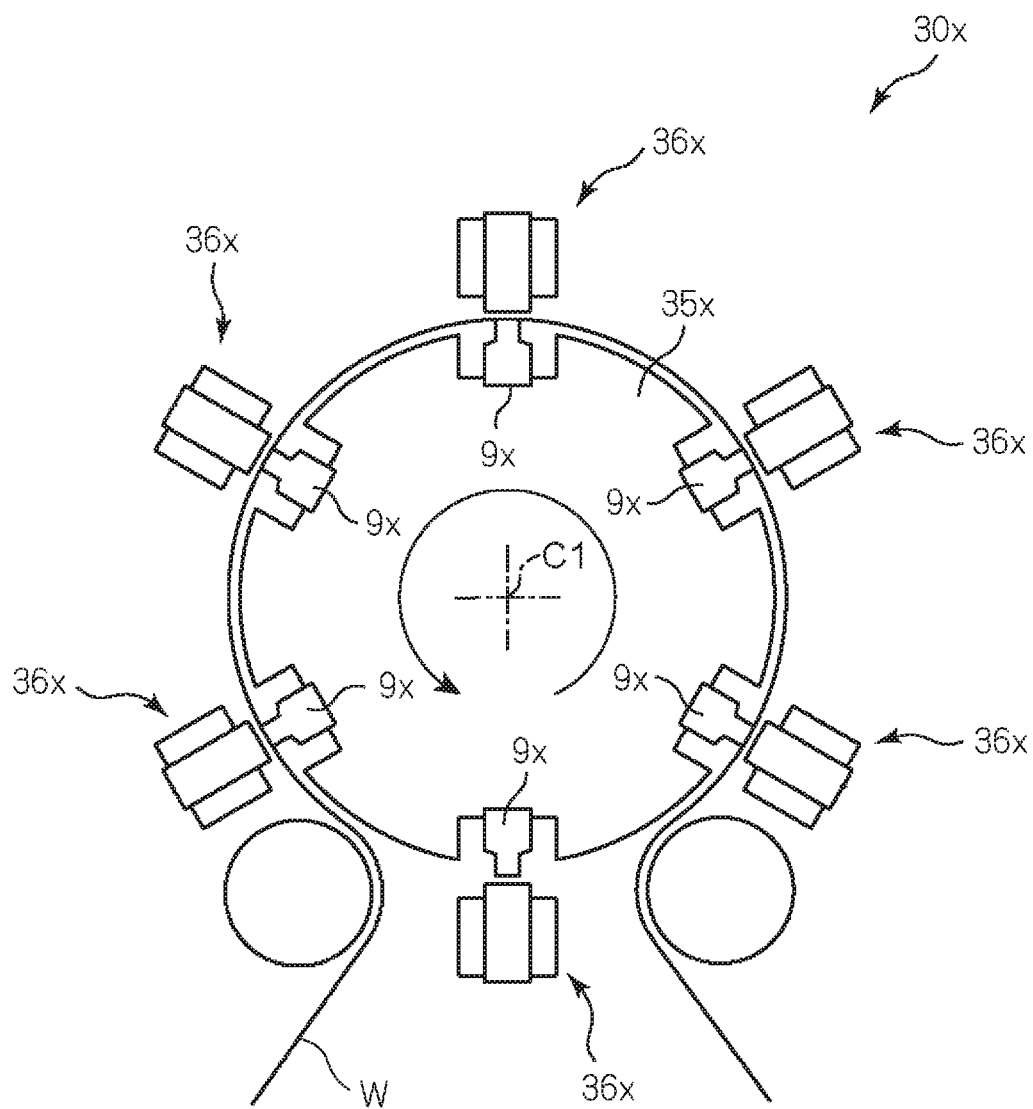
FIG. 10 is a view showing the configuration of an ultrasonic welding device (Conventional example 1).

FIG. 8 is a view illustrating a two-folded work piece W. As shown in FIG. 8, the two-folded work piece W includes a crotch part W1 in which leg holes L are formed and a main body part W2 away from a folding line X.

The two-folded work piece W passes through the introducing roller 50 and is moved along the drum 35 of the ultrasonic welding device 30b and then passes through the discharging roller 51 in the state in which the crotch part W1 is held between the endless belts 40 and 42. As in Embodiments 1 and 2, the main body part W2 of the work piece W passes through the introducing roller 50 without being held between the endless belts 40 and 42, is supported by the work piece support members 35a, and is held between the anvil 38 and the horn 9 of the welding machine 36 to form welded parts S, and then passes through the discharging roller 51.

Since the ultrasonic welding device 30b is provided with the two endless belts 40 and 42, flapping of the crotch part W1 due to a centrifugal force can be prevented. As a result, the processing accuracy of the welded parts is raised.

Summary

As described above, with the ultrasonic welding devices 30, 30a and 30b, it is possible to avoid a defect resulting from welding the part to be welded of the work piece in which there is an abnormality.

The present invention is not limited to the above-mentioned embodiments and can be embodied by variously modifying the embodiments.

For example, although the drum having the cylindrical imaginary surface is used as the support device in the embodiments, it is possible to use a support device having a conveyance surface with an arbitrary shape, such as a linear shape or a U shape, for example, a support device having a conveying belt, in the present invention.

For example, in Embodiment 2, the transducer, the horn, the cylinder and the lever support shaft are fixed to the support member, and the support member is moved in the direction parallel to the rotation center axis of the drum, whereby the horn and the anvil are disposed at positions facing the imaginary surface. In the present invention, however, for example, the horn may be fixed to the drum at the position facing the imaginary surface in advance instead of fixing the horn to the support member, and the anvil may be moved to the position facing the horn by moving the support member.

DESCRIPTION OF REFERENCE NUMERALS AND SIGNS

7 oscillator
8 transducer
9, 9x horn
30, 30a, 30b, 30x ultrasonic welding device
35, 35x drum (support device)
35a work piece support member
35s imaginary surface
36, 36x welding machine
37 contacting/separating mechanism
38 anvil
60 detector
70 protective device
74 controller

The invention claimed is:

1. An ultrasonic welding device comprising:
   a support device configured so as to support a work piece along a predetermined conveyance surface,
   a welding machine including an oscillator for generating an electric signal, a transducer for converting the electric signal to a mechanical vibration, and a horn to which the mechanical vibration is transmitted, the horn being disposed so as to face a part to be welded of the work piece supported along the conveyance surface, and the mechanical vibration being imparted via the horn to the part to be welded, whereby the part to be welded is welded,
   a detector for detecting an abnormality in the part to be welded of the work piece, the detector being disposed further upstream in a conveyance direction of the work piece than the support device, and
   a protective device for prohibiting the welding machine from welding the part to be welded of the work piece in which the abnormality is detected by the detector.

2. The ultrasonic welding device according to claim 1, wherein
   the protective device includes a controller for stopping the oscillator of the welding machine at a time when the horn of the welding machine faces the part to be welded of the work piece in which the abnormality is detected by the detector.

3. The ultrasonic welding device according to claim 1, wherein
   the welding machine includes an anvil disposed so as to face the horn and a contacting/separating mechanism for moving at least either one of the horn and the anvil in a direction away from the other, and
   the protective device includes a controller for controlling the contacting/separating mechanism so that at least either one of the horn and the anvil is moved in the direction away from the other at a time when the horn of the welding machine faces the part to be welded of the work piece in which the abnormality is detected by the detector.

4. The ultrasonic welding device according to claim 1, wherein the ultrasonic welding device is provided with a plurality of welding machines.

5. The ultrasonic welding device according to claim 1, wherein the support device is a drum having work piece support members disposed in a circumferential direction with space therebetween and the work piece support members support the work piece along a part of a cylindrical moving path thereof.

6. An ultrasonic welding method comprising:
  a conveying process for conveying a work piece while supporting the work piece along a conveyance surface and for disposing a part to be welded of the work piece between a horn and an anvil,
  a welding process for holding the part to be welded of the work piece between the horn and the anvil and for imparting a mechanical vibration that is converted from an electric signal generated by an oscillator to the part to be welded via the horn, thereby welding the part to be welded,
  a detecting process for detecting an abnormality of the part to be welded of the work piece at a position further upstream in a conveyance direction of the work piece than the horn and the anvil, and
  a protecting process for prohibiting the welding of the part to be welded of the work piece in which the abnormality is detected.

7. The ultrasonic welding method according to claim 6, wherein
  the protecting process stops the oscillator when the part to be welded of the work piece in which the abnormality is detected is disposed between the horn and the anvil.

8. The ultrasonic welding method according to claim 6, wherein
  when the part to be welded of the work piece in which the abnormality is detected is disposed between the horn and the anvil, the protecting process prevents the part to be welded from being held between the horn and the anvil by moving at least either one of the horn and the anvil in a direction away from the other.

9. The ultrasonic welding method according to claim 6, wherein
  plural sets, each being composed of the horn, the anvil and the oscillator, are provided.

10. The ultrasonic welding method according to claim 6, wherein
  in the welding process, the conveyance surface is a portion of a cylindrical moving path of the work piece.

11. The ultrasonic welding device according to claim 2, wherein the support device is a drum having work piece support members disposed in a circumferential direction with space therebetween and the work piece support members support the work piece along a part of a cylindrical moving path thereof.

12. The ultrasonic welding device according to claim 3, wherein the support device is a drum having work piece support members disposed in a circumferential direction with space therebetween and the work piece support members support the work piece along a part of a cylindrical moving path thereof.

13. The ultrasonic welding device according to claim 4, wherein the support device is a drum having work piece support members disposed in a circumferential direction with space therebetween and the work piece support members support the work piece along a part of a cylindrical moving path thereof.

14. The ultrasonic welding method according to claim 7, wherein
  in the welding process, the conveyance surface is a portion of a cylindrical moving path of the work piece.

15. The ultrasonic welding method according to claim 8, wherein
  in the welding process, the conveyance surface is a portion of a cylindrical moving path of the work piece.

16. The ultrasonic welding method according to claim 9, wherein
  in the welding process, the conveyance surface is a portion of a cylindrical moving path of the work piece.

17. The ultrasonic welding device according to claim 2, wherein the ultrasonic welding device is provided with a plurality of welding machines.

18. The ultrasonic welding device according to claim 3, wherein the ultrasonic welding device is provided with a plurality of welding machines.

19. The ultrasonic welding method according to claim 7, wherein
  plural sets, each being composed of the horn, the anvil and the oscillator, are provided.

20. The ultrasonic welding method according to claim 8, wherein
  plural sets, each being composed of the horn, the anvil and the oscillator, are provided.

* * * * *